United States Patent
Somaraju et al.

(10) Patent No.: US 8,591,954 B2
(45) Date of Patent: *Nov. 26, 2013

(54) PHOSPHOLIPID-BASED INHALATION SYSTEM

(75) Inventors: Shailaja Somaraju, Catonsville, MD (US); Julie Suman, Baltimore, MD (US); Sudipta Ganguly, Summit, NJ (US); Richard Dalby, Lutherville, MD (US)

(73) Assignee: Next Breath, LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,473

(22) Filed: Jun. 25, 2012

(65) Prior Publication Data

US 2012/0308617 A1    Dec. 6, 2012

Related U.S. Application Data

(63) Continuation of application No. 11/977,932, filed on Oct. 26, 2007, now Pat. No. 8,206,687.

(60) Provisional application No. 60/854,596, filed on Oct. 26, 2006.

(51) Int. Cl.
| | | |
|---|---|---|
| *A61K 9/00* | (2006.01) | |
| *A61K 9/12* | (2006.01) | |
| *A61K 9/14* | (2006.01) | |
| *A61M 11/00* | (2006.01) | |
| *A61M 11/02* | (2006.01) | |
| *A61M 11/04* | (2006.01) | |

(52) U.S. Cl.
USPC ... 424/489; 424/46; 128/200.14; 128/200.21; 128/200.24

(58) Field of Classification Search
USPC .................. 424/46, 489; 128/200.14, 200.21, 128/200.24
See application file for complete search history.

(56) References Cited

U.S. PATENT DOCUMENTS

| | | | |
|---|---|---|---|
| 5,855,913 A | 1/1999 | Hanes et al. | |
| 6,676,930 B2 | 1/2004 | Mautone | |
| 6,921,528 B2 | 7/2005 | Edwards et al. | |
| 6,932,962 B1 | 8/2005 | Backstrom et al. | |
| 6,949,532 B2 | 9/2005 | Sequeira et al. | |
| 7,473,416 B2 | 1/2009 | Hills et al. | |
| 8,206,687 B2 * | 6/2012 | Somaraju et al. ............... | 424/45 |
| 2008/0019926 A1 | 1/2008 | Krafft et al. | |
| 2010/0095963 A1 | 4/2010 | Sharpe et al. | |

OTHER PUBLICATIONS

Steimer et al. Cell culture models of the respiratory tract relevant to pulmonary drug delivery. J. Aerosol Med. 18: 137-182 (2005).
R. Dalby and J. Suman. Inhalation therapy: technological milestones in asthma. Adv. Drug Del. Rev. 55: 779-791 (2003).
S.J. Farr, S.J. Warren, P. Lloyd, J.K. Okikawa, J.A. Schuster, A.M. Rowe, R.M. Rubsamen, and G. Taylor. Comparison of in vitro and in vivo efficiencies of a novel unit-dose liquid aerosol generator and a pressurized metered dose inhaler. Int. J. Pharm. 198: 63-70 (2000).
R.W. Niven. Powders and processing: deagglomerating of a dose of patents and publications. In R.N. Dalby, P. Byron, J. Peart, and S. Farr (eds.), Respiratory Drug Delivery VIII, DHI, Rayleigh, pp. 257-266 (2002).
K.R. Chapman, L. Love, and H. Brubaker. A comparison of breath-actuated and conventional metered-dose inhaler inhalation techniques in elderly subjects. Chest. 104: 1332-1337 (1993).
P. Girodet and M. Molimard. Pharmacological approach to evaluate aerosol pulmonary deposition. J. Aerosol Med. 18: 183-192 (2005).
M. Sakagami. Pulmonary insulin: a critical review of its biopharmaceutics. In R.N. Dalby, P. Byron, J. Peart, and S. Farr (eds.) Respiratory Drug Delivery VIII, DHI, Rayleigh, pp. 69-78 (2002).
G.K. Suresh and R.F. Soll. Lung surfactants for neonatal respiratory syndrome: animal derived or synthetic agents. Pediatr. Drugs. 4: 485-492 (2002).
F.F. Espinosa and R.D. Kamm. Bolus dispersal through lungs in surfactant replacement therapy. J. Appl. Physiol. 86: 391-410 (1999).
R.J. Rodriguez. Management of respiratory distress syndrome: an update. Respir. Care. 48: 279-287 (2003).
K. Fumoto, T. Uchimura, T. Iwasaki, K. Ueda, and H. Hosoya. Phosphorylation of myosin II regulatory light chain is necessary for migration of HeLa cells but not for localization of myosin II at the leading edge. Biochem J. 370: 551-556 (2003).
S.L. Schwindling, M. Faust, and M. Montenarh. Determination of mitotic index by microinjection of fluorescently labeled tubulin. J. Cell Biol. 81: 169-174 (2002).
J.C.M. Stewart. Colormetric determination of phospholipids with ammonium ferrothiocyante. Anal. Biochem. 104: 10-14 (1980).
A.H. Pischtiak, M. Pittroff, and T. Schwarze. Characteristics, supply and use of the hydroflurocarbon HFA 227 and HFA 134a for medical aerosols in past, present and future manufacturers perspectives (2006).
H. Steckel and S. Wehle. A novel formulation technique for metered dose inhaler (MDI) suspensions. Int. J. Pharm. 284: 75-82 (2004).

(Continued)

*Primary Examiner* — James H Alstrum Acevedo
(74) *Attorney, Agent, or Firm* — Whiteford, Taylor & Preston LLP; Joseph L. Morales

(57) ABSTRACT

The present invention includes a method for delivering medications deeper into the lungs and to the medications' pulmonary targets, which include bronchioles and alveoli. A first particularly preferred embodiment of the invention describes the use of two steps for delivery of a medication. In a first step, an aerosolized therapeutic composition or medication is administered into a patient's respiratory tract, wherein the patient may be any animal or human subject. Following the first step, an aerosolized surfactant is administered into the patient's respiratory tract that facilitates delivery of the aerosolized medication of the first step to the medication's pulmonary target. Another embodiment of the present invention contemplates an apparatus for the delivery of an aerosolized surfactant used that facilitates delivery of previously inhaled aerosolized medication.

12 Claims, 9 Drawing Sheets

(56) References Cited

OTHER PUBLICATIONS

T. Kinnarinen, J. Jarvinen, P. Jarho, H. Vihola, J. Hirvonen, and T. Jarvinen. Cyclodextrins in pulmonary drug delivery: in vitro toxicity of cyclodextrins in Calu-3 cells. In R.N. Dalby, P. Byron, J. Pearl, J.D. Suman and S. Farr (eds.), Respiratory Drug Delivery IX, DHI, River Grove, pp. 773-776 (2004).

Ganguly et al. Phospholipid-Induced in Vivo Particle Migration to Enhance Pulmonary Deposition. J. of Aerosol Medicine and Pulmonary Drug Delivery. 21:4 pp. 343

PHOSPHOLIPID-BASED INHALATION SYSTEM

CROSS REFERENCE TO RELATED APPLICATIONS

This application is a continuation application of U.S. patent application Ser. No. 11/977,932, filed Oct. 26, 2007, now U.S. Pat. No. 8,206,687, issue date Jun. 26, 2012, which claims priority to U.S. Provisional Patent Application Ser. No. 60/854,596 filed Oct. 26, 2006, from which this application also claims priority, each of the above-reference applications is hereby incorporated by reference in its entirety.

BACKGROUND OF THE INVENTION

1. Field of the Invention

This invention generally relates to the field of drug delivery. More particularly, this invention is directed to inhaled medications (for example medications delivered through pressurized metered dose inhalers ("pMDIs") or other inhalers) and the delivery of medications to conducting airways and alveoli in a respiratory system.

2. Background of the Invention

Inhaled medications are commonly used to target drugs to the lungs in the treatment and prevention of various medical conditions. A. Steimer, E. Haltner, & C. M. Lehr, *Cell Culture Models of the Respiratory Tract Relevant to Pulmonary Drug Delivery*, 18 J. Aerosol Med. 137 (2005); R. Dalby & J. Suman, *Inhalation Therapy: Technological Milestones in Asthma*, 55 Adv. Drug. Del. Rev. 779 (2003). Drugs administered through the pulmonary route either act locally in the lungs or enter the systemic circulation following dissolution and absorption. Numerous particle and device engineering approaches have been attempted to incorporate drugs into small particles or make small pure drug particles for delivery to the most desirable lung locations. Such approaches include modifications to nebulizers, pressurized metered dose inhalers (pMDIs), active or passive dry powder inhalers (DPIs), or changes to the nature of the particles themselves. The ultimate objectives of particle and device engineering are to generate small slow moving particles with favorable aerodynamic properties. S. J. Farr, S. J. Warren, P. Lloyd, J. K. Okikawa, J. A. Schuster, A. M. Rowe, R. M. Rubsamen & G. Taylor, *Comparison of in Vitro and in Vivo Efficiencies of a Novel Unit-Dose Liquid Aerosol Generator and a Pressurized Metered Dose Inhaler*, 198 Int. J. Pharm. 63 (2000); VIII R. W. Niven, *Respiratory Drug Delivery, Powders and Processing: Deagglomerating of a Dose of Patents and Publications* 257-266 (R. N. Dalby, P. Byron, J. Peart, & S. Farr eds., DHI, Rayleigh 2002); K. R. Chapman, L. Love, & H. Brubaker, *A Comparison of Breath-Actuated and Conventional Metered-Dose Inhaler Inhalation Techniques in Elderly Subjects*, 104 Chest. 1332 (1993).

The fraction of drug delivered to the bronchial tree may be cleared by mucociliary transport and absorption through the airway epithelium into the systemic circulation. Thus, after initial deposition, drug particles do not migrate deeper into the lung. The opposite occurs: once particles encounter the fluid lining of the lung; they are either absorbed or transported to the larger airways of the lung by lung clearance mechanisms. Drug reaching the target region (which may be conducting airways or alveoli) of the lung following pulmonary inhalation (expressed as bioavailability or a deposition fraction) is often estimated at less than 10%. VIII M. Sakagami, *Respiratory Drug Delivery, Pulmonary Insulin: a Critical Review of Its Biopharmaceutics* 69-78 (R. N. Dalby, P. Byron, J. Peart, & S. Farr eds., DHI, Rayleigh 2002).

Following premature births, structurally immature and surfactant-deficient lungs containing reduced levels of pulmonary phospholipids are sometimes treated with natural and synthetic exogenous surfactants (treatment of Respiratory Distress Syndrome RDS). G. K. Suresh & R. F. Soll, *Lung Surfactants for Neonatal Respiratory Syndrome: Animal Derived or Synthetic Agents*, 4 Pediatr. Drugs. 485 (2002). These exogenous surfactants are complex colloidal dispersions composed primarily of phospholipids. They may contain additional components such as fatty acids, triglycerides and spreading agents. The dose of surfactant is relatively high and is administered to premature infants affected with RDS via endotracheal or intratracheal instillation wherein the surfactant is dripped directly into the bronchioles.

After instillation, the surfactant is distributed throughout the airways and the bolus advances distally while coating the airway walls with a thin layer of surfactant. F. F. Espinosa & R. D. Kamm, *Bolus Dispersal Through Lungs in Surfactant Replacement Therapy*, 86 J. Appl. Physiol. 391 (1999). The thickness of the coat of surfactant is dependent on surfactant concentration, viscosity and surface tension. In addition, a "reservoir" of surfactant remains in the larger airways as the surfactant expands into the lungs. Surface tension gradients draw exogenous surfactant distally to high surface tension locations thereby allowing surfactant to reach the alveoli.

FDA approval and continuous commercial availability of exogenous surfactants and their use in critically ill neonatal patients confirms the safety of phospholipid administration to the human respiratory tract. Their mode of administration (tracheal instillation) and site of action (alveolar spaces) confirms that the active components of these surfactant mixtures successfully spread from the trachea to the alveoli to exert their beneficial effect. R. J. Rodriguez, *Management of Respiratory Distress Syndrome: An Update*, 48 Respir. Care. 279 (2003).

SUMMARY OF THE INVENTION

The present invention provides a method for delivering deposited drug particles or droplets containing dissolved drug deeper into the respiratory tract or human or animal subjects in front of the spreading surfactant layer, thus increasing the fraction of drug that reaches the desirable targets in the bronchioles and alveolar spaces of the lung. One particularly preferred embodiment of the invention is a method for delivering medications or particles to pulmonary targets where a first step of administering an aerosolized (inhaled) medication into a patient's respiratory tract is followed by a second step of administering an aerosolized (inhaled) surfactant into the patient's respiratory tract. The second step facilitates deeper lung penetration of the aerosolized medication administered in the first step by pushing the medication deeper into the lungs and closer to the medication's pulmonary target. Consequently, the patient inhales his or her medication from an existing inhaler (such as a pMDI) containing the desired medication such that drug (or drug in droplets) deposits on the luminal surface. The location of deposition of the particles depends on inhaler characteristics and patient technique. The patient immediately inhales a dose of surfactant from a second inhaler containing surfactant particles (e.g., phospholipid molecules) or droplets larger than the drug particles. The larger surfactant particles deposit higher in the airway and, as the surfactant dissolves and spreads deeper into the respiratory tract, drug particles are pushed deeper into the lungs ahead of the expanding surfactant layer.

A second aspect of the present invention contemplates an apparatus for delivery of aerosolized surfactants to be administered after initial inhalation of an aerosolized medication, comprising a pressurized meter dose inhaler, DPI or nebulizer formulation. For example, the pressurized meter dose inhaler formulation would comprise a surfactant that facilitates delivery of the aerosolized medication and a propellant.

A further aspect of the present invention includes a method for selecting a surfactant formulation that facilitates the delivery of an aerosolized medication, comprising determining an aerodynamic particle size distribution for a surfactant formulation. The aerodynamic particle size distribution is determined using a method wherein a surfactant formulation is delivered into a dome connected to an impactor. The surfactant that deposits on the impactor is then collected and its concentration measured.

Yet a further aspect of the present invention comprises a method of selecting molecules to act as surfactants for delivery of aerosolized medications, comprising monitoring migration of latex beads placed on tissue cells after application of a surfactant formulation.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION

The invention summarized above may be better understood by referring to the following description, which should be read in conjunction with the accompanying drawings and claims. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
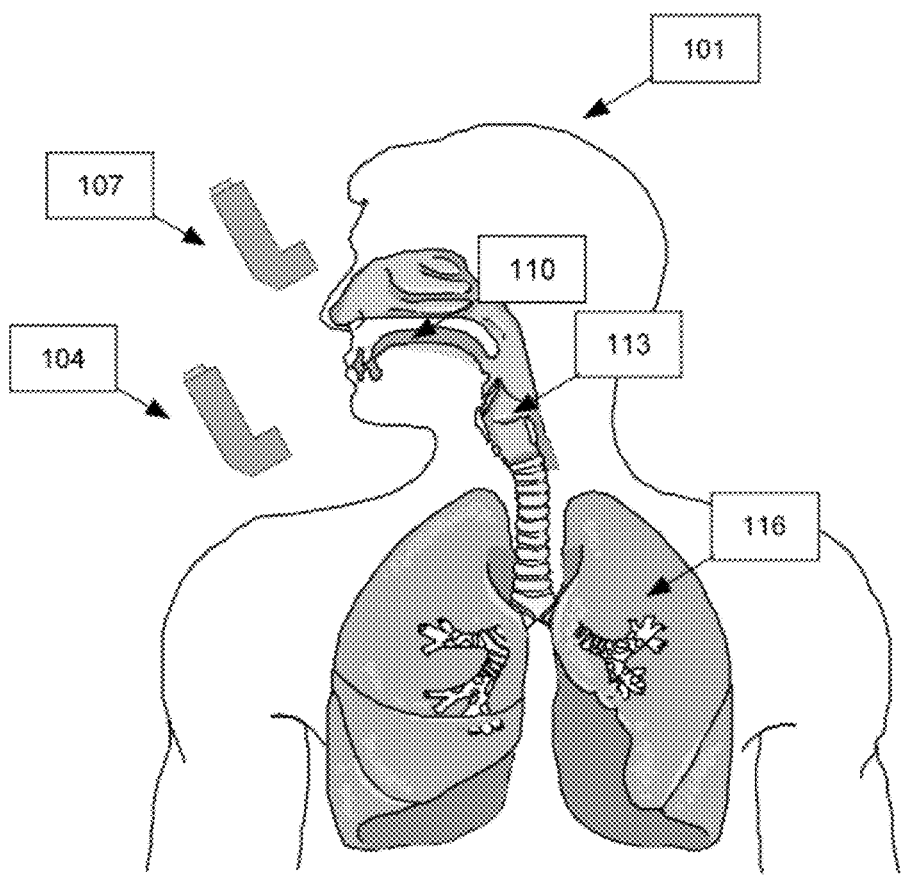
FIG. 1 provides a graphical overview of a method of delivering medications to the lungs.

The present invention includes a method for delivering medications deeper into the lungs and to the medications' pulmonary targets, which include bronchioles and alveoli. It is contemplated that a medication includes any particle, molecule or composition administered to a subject, human or animal, to achieve any desired result. A first particularly preferred embodiment of the invention describes the use of two steps for delivery of a medication. In a first step, an aerosolized medication is administered into a patient's respiratory tract, wherein the patient may be any animal or human subject. Following the first step, an aerosolized surfactant is administered into the patient's respiratory tract that facilitates delivery of the aerosolized medication of the first step to the medication's pulmonary target. For example, as shown in FIG. 1, the patient 101 inhales his or her medication from a container 104, such as a pMDI. It is contemplated that, throughout this specification, the term "particle" or "particles" includes mixtures containing the medication or surfactant, droplets in which the medications or surfactants have been dissolved, solid medication or surfactant particles, and any other composition contemplated by one skilled in the art to contain the medication or surfactant being administered to the patient. The particles or droplets deposit on the luminal surface 113. The location for deposit of the particles depends on the inhaler characteristics and patient technique. The patient then inhales a dose of the aerosolized surfactant from a second inhaler 107. The surfactant contains phospholipid particles that push the medication to its pulmonary target. The phospholipid molecules, packed in aerosolized particles larger than those in which the medication is delivered, deposit at a higher location in the airway 110 and slide down the oropharyngeal region 113 creating a gradient and pushing the smaller particles, containing the medications, deeper into the lungs 116. The same effect can be obtained through the use of a tandem inhaler apparatus, or any other application that allows the smaller particles containing the medications to be delivered first, followed by the larger particles containing a surfactant that includes phospholipid "chaser" molecules.

The surfactant to be used in delivering medications can be packaged in a container 104 (such as a pMDI, nebulizer, dry powder inhaler, or any other aerosolized delivery mechanism) comprising a propellant and a surfactant formulation that facilitates delivery of the medication. For example, surfactant formulations to be used in the second pMDI under this method may include various volumes of a surfactant, e.g. PTC or Survanta®, containing a volume of phospholipids, e.g., 25 mg/mL, packaged into glass pMDI canisters and freeze-dried at an appropriate temperature, e.g., −80° C., to remove water. The freeze-dried product can be dispersed using anhydrous ethanol in a desired volume, e.g., 1 mL. The pMDIs are then crimped with appropriate nitrile valves, such as 63 μL (Bespak plc, Milton Keynes, UK), and pressure filled with an appropriate quantity of CFC-12, or other suitable propellant including CFC-11, CFC-114, HFA-227, and HFA-134, in some cases approximately 4 gms, to achieve an optimal phospholipid concentration range, which can be 0.5-6 mg/mL. HFA-227 can also be used as the propellant (theoretical phospholipid emitted dose=100 ±5 μg per spray). When using HFA-227 the formulation can contain various amounts of anhydrous ethanol (5% to 31% w/w), PEG-400 (2% to 15% w/w) and HP-β-CD (0.3% to 1.5% w/w). Suspension physical stability can be assessed visually and formulations with instant coagulation-precipitation can be rejected from use. One of such assessments is described in the following Table I:

TABLE I

Formulation of HFA-227 containing Survanta ® pMDIs; emitted dose of phospholipid was 100 ± 5 μg/spray. Precipitation/coagulation can be assessed visually. Large number of '+' depicts instant precipitation and in some cases sticking to the walls of the container. Six formulations selected for aerodynamic particle sizing were Formulation Nos., 3, 4, 5, 7, 8 and 11 (shaded cells).

| Formulation No. | Ethanol (% w/w) | HFA-227 (% w/w) | PEG-400 (% w/w) | HP-β-CD (% w/w) | Theoretical Vapor Pressure (mm Hg)* | Precipitation/Coagulation |
|---|---|---|---|---|---|---|
| 1 | 45.9 | 54.1 | — | — | 741.60 | − |
| 2 | 40.7 | 59.3 | — | — | 858.56 | − |
| 3 | 31.5 | 68.5 | — | — | 1112.4 | − |
| 4 | 20.8 | 79.2 | — | — | 1506.8 | + |
| 5 | 9.36 | 90.6 | — | — | 2129.4 | ++ |
| 6 | 8.77 | 91.0 | — | 0.22 | 2168.7 | +++++ |
| 7 | 6.56 | 93.4 | — | — | 2331.5 | +++ |
| 8 | 7.87 | 78.1 | 14.0 | — | 2030.4 | ++ |
| 9 | 6.17 | 82.1 | 11.0 | 0.78 | 2200.3 | +++++ |
| 10 | 6.91 | 91.9 | 1.23 | — | 2288.1 | ++++ |
| 11 | 4.57 | 82.4 | 13.0 | — | 2306.4 | +++ |

*Theoretical vapor pressures can be calculated based on vapor pressure of ethanol = 44.6 mm Hg, vapor pressure of HFA-227 = 2925 mm Hg and vapor pressure of PEG-400 = 0.01 mm Hg at 25° C.

While the above description particularly recites the use of CFC-12 and HFA-227, one of ordinary skill in the art will recognize that other suitable propellants or carrier mediums may likewise be used without departing from the spirit and scope of the instant invention. For example, CFC-11, CFC-114, HFA-134 and other propellants may also be used. In addition, it is contemplated that different methods of aerosolizing molecules may be used, such as DPIs, nebulizers, and others.

Appropriate formulations can be selected based on practical considerations of theoretical vapor pressures and sedimentation times. For example, in one embodiment of this invention six formulations were selected with a sedimentation time of at least 3 minutes. After the formulations are selected, aerodynamic particle size can be determined. Formulations containing the desired surfactant that yield administered particles slightly larger than those generated by drug-containing inhalers can be further used to determine the effect of particle migration on tissue cells such as A549 cells using the semi-automated detection technique described below. It is also contemplated that different types of cells may be utilized to determine surfactant properties.

The aerodynamic particle size distribution, as used herein, corresponds to the median size of the particles, either the surfactant particles or the medication particles. It can be assessed using two different methods: the USP Throat Method or the "Dome" Method. In the USP throat method, a cascade impactor such as the eight-stage Andersen Cascade Impactor (ACI; MSP Corp., Shoreview, Minn.) can be used (see FIG. 2, 204) and operated at an appropriate flow-rate, such as 28.3 L/min±5% (flow meter from Sierra Instr. Inc., Monterey, Calif.). In one embodiment of this method, the standard USP induction port (throat) with an internal volume of 60 mL can be employed. The pMDIs prepared for this purpose can then be spiked with a known amount of albuterol (Cipla Ltd., India) for quantification. In vitro deposition of albuterol administered from the pMDI represents that of the phospholipid used because albuterol is present as an ethanolic solution along with the phospholipid. Initially, the pMDIs can be primed by firing 3 shots to the waste. The next 10 shots, with an interval between shots of, for example, 30 seconds, are then made to the impactor. After the last dose of phospholipid is fired, the inhaler is removed from the impactor and the valve stem and actuator are rinsed with the appropriate solvent, for example 10 mL of chromatographic mobile phase. The impactor and throat are disassembled and each plate and filter rinsed in a similar manner with 10 mL of the solvent. Albuterol concentrations are quantified by high performance liquid chromatography (HPLC) as described below. Each pMDI particle size determination can be carried out in triplicate or as many times as needed to obtain a reliable determination. If the USP throat method reveals high throat deposition of the selected formulations and thus mass of particle deposits on the upper stages of 0 to 2 (cut-off diameter: 9 μm to 4.7 μm) can not be assessed, the "Dome" method may be used as described below.

Figure 2:
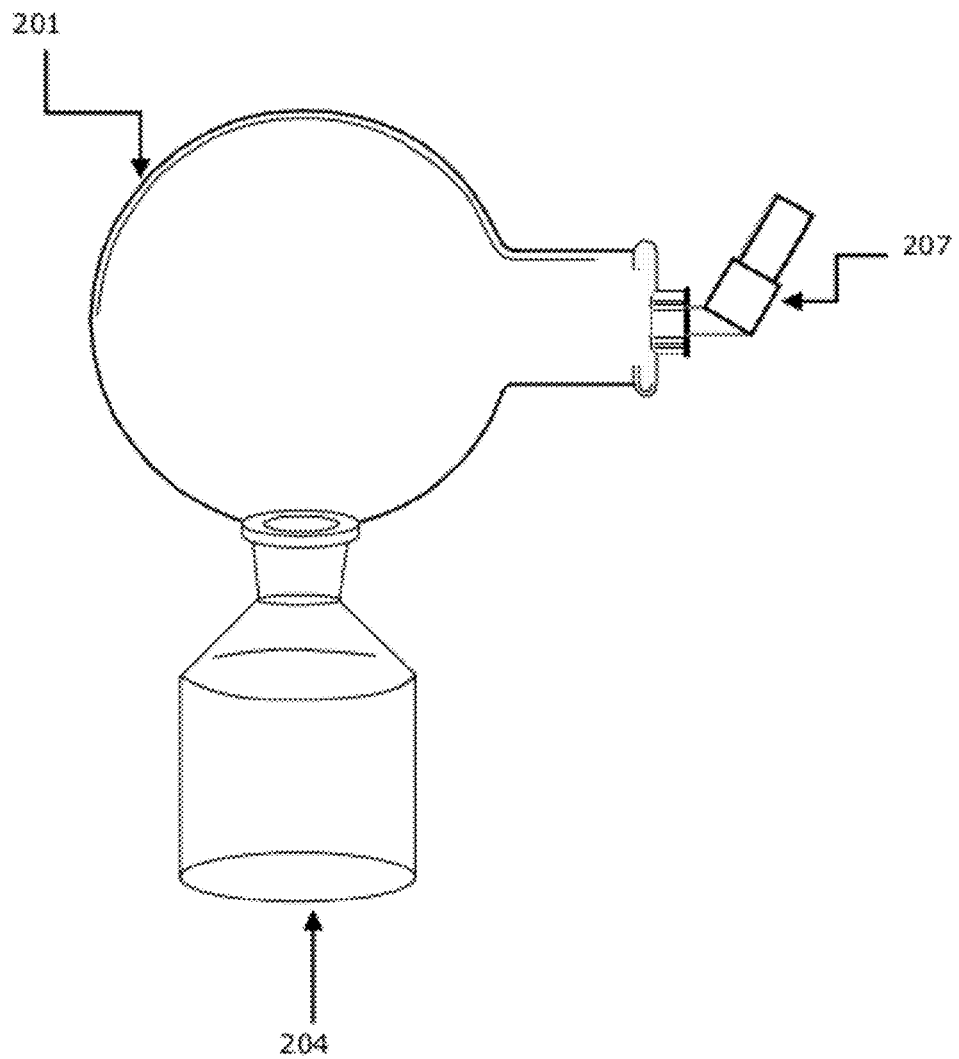
FIG. 2 describes a modified Andersen Cascade Impactor "ACI" system, the "dome" method, used to determine the aerodynamic particle size of surfactant formulation. The "dome" 201 has a capacity of approximately 15 L and is attached on top of the ACI 204. Aerodynamic size of aerosolized particles from a pMDI formulation 207 is measured consecutively.
Figure 3:
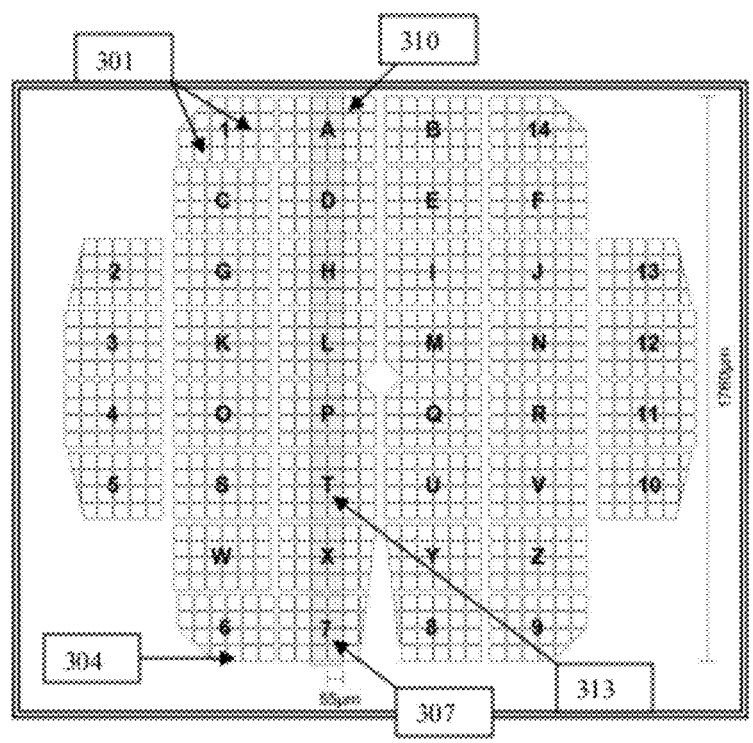
FIG. 3 displays a sample of a microgrid used to count and monitor movement of latex beads as a tool for identifying appropriate pMDI formulations. Location 7 307 is near the point of surfactant application and location A 310 is furthest away within a counting lane 313 (shaded region). Each small grid square 301 represents 55 $\mu m^2$.

The "Dome" method, as shown in FIG. 2, is a modified aerodynamic sizing method that eliminates the USP throat and replaces it with a round flask ("dome") 201, which may have a capacity of approximately 15 L, or other capacities which allow for the quantification of particles. Mass of drug deposited on each stage of the impactor 204 can be determined using the previous method. The "dome" method can be validated by performing deposition studies with a commercially available marketed formulation of albuterol (Ventolin®-HFA; GlaxoSmithKline, Research Triangle Park, N.C.) and comparing the aerodynamic distribution profiles with that obtained using the USP throat method.

Albuterol, deposited on the ACI stages, may be quantified using HPLC (Hitachi Ltd., Tokyo, Japan). The chromatographic separation may be achieved on a number of columns, for example the Spherex C-18, 250×4.6 mm column (Phenomenex, Torrance, Calif.) with UV detection at 276 nm. The mobile phase may consist of deionized distilled water (58% v/v), acetonitrile (40% v/v), glacial acetic acid (2% v/v) and heptane sulfonic acid sodium (0.065% w/v) operated at a flow rate of 1.0 mL/min or other appropriate concentrations of mobile phase components that facilitate the elution and quantification of the surfactant. Using this method, Albuterol elutes at 3.6 mins.

Figure 6:
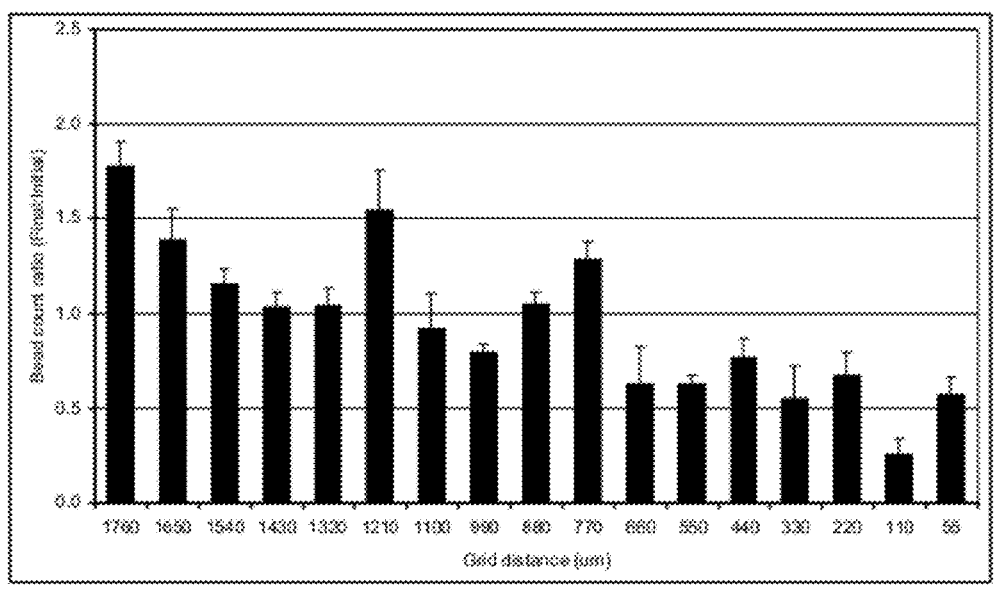
FIG. 6 demonstrates results of the procedure as shown in FIG. 5 utilizing a different surfactant. Particle migration on A549 cell surface on application of Survanta® (Abbott Laboratories, Corp., Abbott Park, Ill. 60064) as monitored using CELLocate microgrid system, plotted as a function of bead count ratio (Final:Initial). Phospholipid was applied on the 55 μm grid distance end (location 7 307) and latex beads migrated away towards the 1760 μm end. Data represent mean±S.D. of triplicate experiments.

A particularly preferred embodiment of the present invention comprises the identification of molecules to be used in the pMDI to push the medication deeper into the lungs. For this purpose an in vitro technique to visualize and monitor migration of latex beads placed on tissue cells after application of the appropriate surfactant may be used. As shown in FIG. 3, commercially available coverslips containing micro-grids 301 have been used, for example, in locating and refinding individual cells or cell groups, determination of cell division indices, measurement of cell growth and cytotaxis and estimation of cell numbers. K. Fumoto, T. Uchimura, T. Iwasaki, K. Ueda & H. Hosoya, *Phosphorylation of Myosin II Regulatory Light Chain is Necessary for Migration of HeLa Cells but not for Localization of Myosin II at the Leading Edge,* 370 Biochem. J. 551 (2003); S. L. Schwindling, M. Faust & M. Montenarh, *Determination of Mitotic Index by Microinjection of Fluorescently Labeled Tubulin,* 81 J. Cell Biol. 169 (2002). One such coverslip microgrid is the CEL-Locate® gridded coverslip shown in FIG. 3. The microgrid coverslips can be used to monitor and quantify bead movement on cell surfaces reflecting similar characteristics to tracheal and pulmonary tissues. For example, A549 cells may be cultured in sterile growth media containing DMEM, 10% FBS and 1% penicillin-streptomycin at 37° C. and 5% $CO_2$, or other appropriate growth media conducive to regular development of the cells. A portion of the cells is added onto the gridded coverslips 301 and incubated as explained previously until confluence is established (~48hours). Latex beads (4.5±0.28 μm in diameter) is then be applied uniformly to the coverslip shown in FIG. 3 using a thin circular ring, and the number of beads in each position can be counted using optical microscopy, such as the Nikon E800, Nikon Instr. Inc., Melville, N.Y., at 400× magnification. After the beads are placed on the coverslip 301, the desired surfactant can be applied utilizing the modified V-shaped 401 adaptor shown on FIG. 4.

A rapid method of analysis can be employed to determine the amount of phospholipids passing through the slit of the V-shaped adaptor shown in FIG. 4 and depositing on the coverslip based on complex formation between ammonium ferrothiocyanate and phospholipids. J. C. M Stewart, *Colorimetric Determination of Phospholipids with Ammonium Ferrothiocyanate,* 104 Anal. Biochem. 10 (1980). A standard solution of ammonium ferrothiocyanate can be prepared by dissolving 27.03 gms of ferric chloride hexahydrate and 30.4 gms of ammonium thiocyanate in 1 L of deionized distilled water. A solution of 10 mg of PTC in 100 mL chloroform may be prepared. Triplicate volumes of this solution, between 0.1 and 2 mL, may be removed to set-up a calibration plot, added to 2 mL ammonium ferrothiocyanate solution in a test tube and enough chloroform to make the final volume of 2 mL. The biphasic mixture is vortexed for 30 seconds and after separation, absorbance of the lower chloroform phase is measured at $\lambda_{max}$=464 nm (Genesys2 UV Spectrophotometer; Spectronic Instr., Rochester, N.Y.). This method allows measurements of phospholipids in the range of 10 μg to 200 μg.

pMDI-delivered phospholipids passing through the slit are dissolved in 2 mL chloroform and added to 2 mL ammonium ferrothiocyanate solution. The mixture is vortexed, absorbance of the chloroform layer measured and phospholipid amount quantified based on the linear calibration plot. The analysis can also be employed to determine mass balance of actuated phospholipids for ACI quantification and to validate the assumption that albuterol deposition is an appropriate measure of phospholipid aerodynamic distribution.

Phosphatidylcholine (PTC) represents at least 60% of both endogenous and exogenous surfactants by weight and can be used as the model surfactant to study particle movement and establish cell models. Any number of phospholipids can be used as surfactants to drive medications deeper into the lungs. One example of such phospholipids is a natural exogenous surfactant, Survanta® (beractant), that can be used for achieving the desired result. Surfactant (10-15μL of PTC, Survanta®, or any other target surfactant) may be added as a narrow band to one end of the grid 304 utilizing the V-shaped 401 apparatus shown on FIG. 4. The movement of latex beads may then be monitored by counting the beads before adding the surfactant and then again after allowing the surfactant to spread for a period of time (for example 10 seconds). Sterile water can be used as a control.

The above mentioned surfactant effect mechanism can be automated. Automation allows one to determine the effect of the chosen surfactant, e.g. PTC or Survanta®, formulation variables on particle migration and reduce variables associated with the manual microgrid counting system. The semi-automated detection system can comprise an inverted optical microscopic system (e.g., Nikon TE-2000 with image acquisition software, Nikon Instr. Inc., Melville, N.Y.) with an automated stage controller system (e.g., Bioprecision XY-stage, Ludl Electronic Products Ltd., Hawthorne, N.Y.). The effect of pMDI-delivered surfactant, e.g., PTC, Survanta®, on latex bead movement can be determined using the above cell model. As shown in FIGS. 3 and 4, surfactant is deposited in a narrow band 304 at only one edge of an ordinary coverslip 410 by spraying each pMDI formulation through the V-shaped adaptor 401 with a narrow slit 407 at the apex. FIG. 5 shows an example of the results that can be obtained after using this procedure. Beads in 220 $\mu m^2$ virtual square grids along a 220×11,000 μm lane (50 grids in total), predefined using the automated stage controller coupled to the microscope, can be counted and quantified, before (initial) and after (final) application of surfactant. Bead migration along an extended lane can then be monitored.

On completion of each use of the system described above, the coverslips can be treated, for example, with 25 μL of trypan blue (0.5%) and visualized under the microscope to check for cell viability. Other methods for determining cell viability may be used. Viable cells, given their intact plasma membranes, exclude the trypan blue stain whereas nonviable, membrane-permeable cells, stain dark blue. As a positive control for trypan blue uptake, prior to adding trypan blue solution, cells grown on a coverslip can be incubated in a solution of 0.2% Triton X-100 in phosphate buffer saline (pH~7.4) for 1-2 mins and the above staining procedure can be performed.

In one example of the application of a particular aspect of this invention, the latex beads (4.5±0.28 μm in diameter) can be shown to significantly migrate on the A549 luminal cell surface upon addition of PTC—away from the point of application ($p<0.05$, ANOVA). Beads in the cell counting lane can be quantified before (Initial position) and after (Final position) application of surfactant or control, and plotted as a ratio of Final:Initial counts, at each distance from the point of surfactant application as shown on FIG. 6. The CELLocate® microgrid counting system can be used, and fewer beads can be observed in "location 7" 307 (near which the surfactant was applied) and higher numbers can be seen in "location A" 310 (furthest observable distance from the surfactant application point). From the plot, these locations can represent regions near the 110 μm and 1650 μm grid length respectively.

Figure 4:
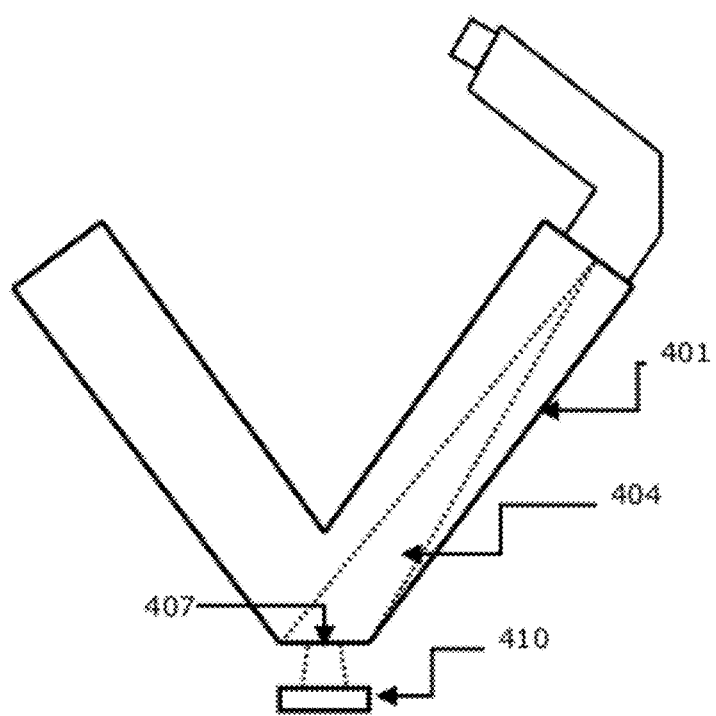
FIG. 4 provides a representation of a V-adaptor used to apply phospholipids to the microgrid shown on FIG. 3: V-piece 401, pMDI spray 404, Slit/opening 407 for spray passage and Coverslip 410.
Figure 5:
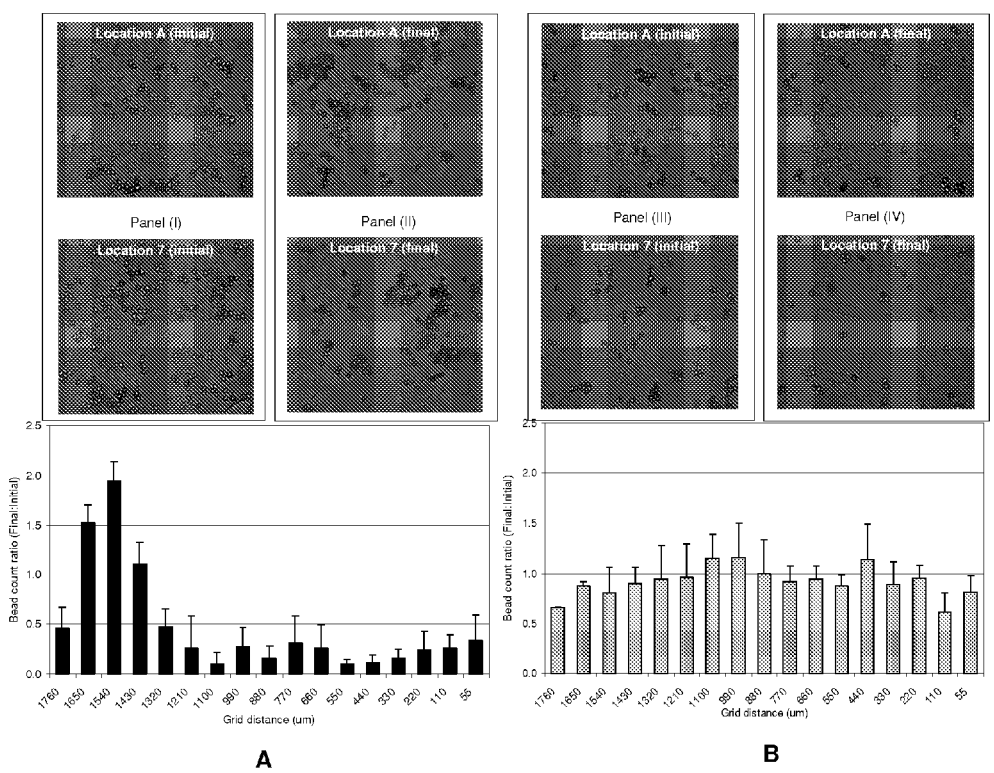
FIG. 5 displays an example of results that can be obtained using the bead migration procedure. (A) Panel (I) shows a 4.5 μm bead distribution before (Initial) application of phosphatidylcholine (PTC) on representative grids at location A 310 (1650 μm grid distance) and location 7 307 (110 μm grid distance). Panel (II) shows bead distribution after (Final) application of PTC on representative grids at location A 310 and location 7 307. (B) Panel (III) shows a 4.5 μm bead distribution before (Initial) application of water (control) on representative grids at location A 310 and location 7 307. Panel (IV) shows bead distribution after (Final) application of water on representative grids at location A 310 and location 7 307. The plots represent bead count ratio (Final:Initial) as a function of grid distance. These show significant migration of latex beads on application of PTC as the surfactant. However, no such migration was observed when water was used as the control. Vertical bars represent mean±S.D. of triplicate experiments. Similar pictures and graphs can be obtained using this method with any prospective surfactant formulation.
Figure 7:
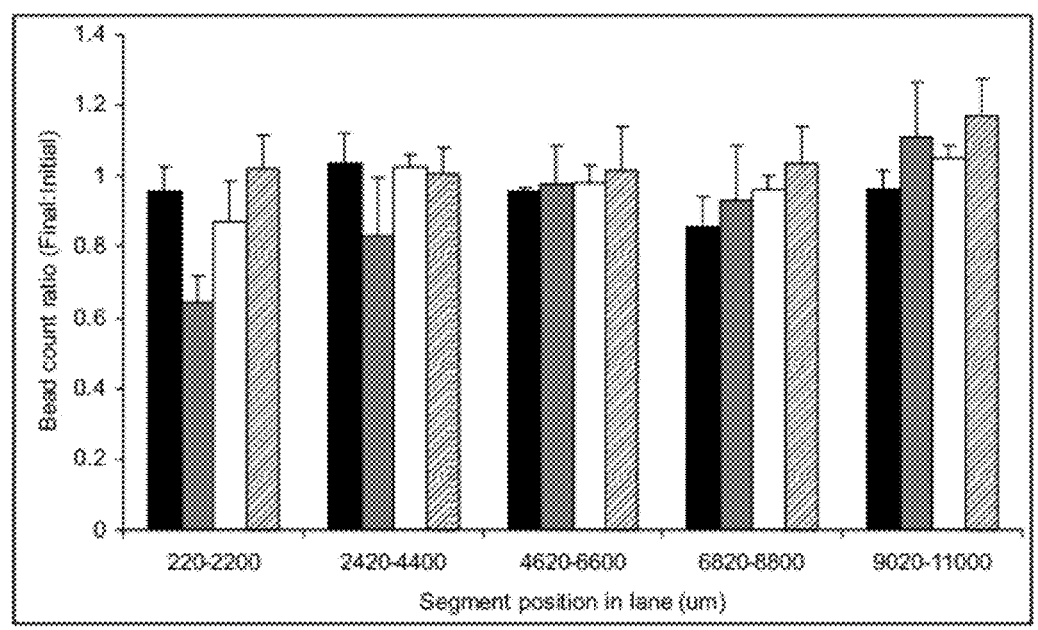
FIG. 7 describes another modification of the bead migration procedure described in FIG. 5, where the effect of the surfactant concentration on migration is quantified. The latex bead count ratio is plotted as a function of grouped segment position demonstrating the concentration effect of CFC-12 pMDI-delivered Survanta® on particle migration across an alveolar cell surface, measured using the semi-automated system. pMDI-delivered Survanta® was applied near the 220 μm segment location. pMDI-delivered Survanta® 0.6 mg/mL ■=72 μg of administered phospholipid; pMDI-delivered Survanta® 1.3 mg/mL ▨ =163 μg of administered phospholipid; pMDI-delivered Survanta® 1.8 mg/mL □=221 μg of administered phospholipid; pMDI-delivered Survanta® 6.2 mg/mL ▧ =786 μg of administered phospholipids. Data represent mean±S.D. of triplicate observations with each pMDI actuated twice per observation.

The technique can be repeated using other surfactants such as Survanta® as shown on FIG. 4. The use of Survanta® at an original concentration of 25 mg/mL of phospholipids can be shown to result in significant migration of beads across the counting lane. The appropriate surfactant such as Survanta® may be pressure filled into pMDIs containing CFC-12, or other appropriate pressurizing agent, and ethanol as the co-solvent. Upon application of pMDI-formulated Survanta® (containing CFC-12 as the propellant) using the V-shaped adaptor 401, a similar migration of particles can be observed. The semi-automated detection technique can be employed to quantify particle migration across the cell surface as described earlier. Virtual square grids of 220 μm² along a 220×11,000 μm lane (50 grids in total), or other distribution of grids, can be predefined using the automated stage controller coupled to the microscope. Beads can be counted and quantified before (Initial) and after (Final) application of the desired surfactant. To reduce grid to grid variability in counts (noise) and summarize data more efficiently, the grids from the semi-automated counting system may be accumulated into groups. In some cases it may be appropriate to create groups of ten grids (representing 220×2,200 μm segments of the counting lane) and plotted as a function of bead count ratio (Final bead count in segment/Initial bead count in same segment), as shown in FIG. 7. This plot demonstrates how bead migration across the cell layer is dependent upon the dose of surfactant emitted by the pMDI. Significant bead movement may be observed using pMDIs delivering different concentrations of phospholipids. In one embodiment of this invention such concentration was equal to 221 μg of phospholipids (from an pMDI containing 1.8 mg/mL phospholipid, $p<0.05$).

The amount of phospholipid actually passing through the slit 407 of the V-shaped adaptor 401 and depositing on the coverslip 410 can be quantified based on the colorimetric assay as explained previously. Red inorganic ammonium ferrothiocyanate is insoluble in chloroform, but forms a colored complex with phospholipids, which are freely soluble in chloroform and can be quantified. The composition of this complex has been determined to be phospholipid:$Fe(SCN)_3$::1:1. J. C. M Stewart, *Colorimetric Determination of Phospholipids with Ammonium Ferrothiocyanate*, 104 Anal. Biochem. 10 (1980). In one embodiment of the invention, in which pMDI contains 1.3 mg/mL phospholipid, the amount of phospholipid deposited can be calculated to be 16±3.2 μg/spray; and for pMDI containing 1.8 mg/mL phospholipid, the deposited amount can be 27±0.8 μg/spray.

Due to practical considerations of non-ozone depleting HFA replacing the ozone depleting CFC propellants in pMDIs, a preferred embodiment of the invention utilizes ozone friendly HFA pMDIs. One example of such ozone friendly pMDIs contains HFA-227 as the propellant of choice for reformulating the phospholipid chaser pMDIs. The dielectric constant for HFA-227 at 25° C. is 3.94. A. H. Pischtiak, M. Pittroff, & T. Schwarze, *Characteristics, Supply and Use of the Hydroflurocarbon HFA 227 and HFA 134a for Medical Aerosols in Past, Present and Future-Manufacturers Perspectives*, www.solvay-fluor.com/docroot/fluor/static_files/attachments/characteristics.pdf (accessed Jun. 26, 2006). HFA-227 is, therefore, a slightly polar substance, a property that can be utilized to determine the dissolving behavior of HFA with the desired surfactants.

It is contemplated that the concentration of phospholipid may range between 0.001 mg and 50 mg per spray, and preferably between 0.01 mg and 10 mg per spray. For example, in a preferred embodiment of this invention CFC-12 containing pMDIs with an effective emitted dose of phospholipid that produced significant particle migration can be found to range within 0.082 mg to 0.111 mg per spray. pMDIs can also be pressure filled with HFA-227 and other excipients to achieve a theoretical emitted dose of phospholipid equal to, for example, 0.100±0.005 mg per spray.

Anhydrous ethanol can be employed as the co-solvent to enhance the suspension stability of the pMDIs. Increasing concentrations from 5% w/w to 31% w/w of ethanol can enhance the physical stability and reduced coagulation and precipitation of phospholipids. At concentrations below 10% w/w of ethanol, secondary stabilizing agents such as PEG-400 or HP-β-CD can be used. Both HP-β-CD and PEG are well-established pharmaceutical excipients and are approved for intravenous administration. H. Steckel & S. Wehle, *A Novel Formulation Technique for Metered Dose Inhaler (pMDI) Suspensions*, 284 Int. J. Pharm. 75 (2004).

In a preferred embodiment of the invention the ACI with the USP throat and the "dome" method for the selected formulations (with albuterol as the marker for phospholipid deposition) can be used and the results can be summarized as shown in Table II. For the USP throat method, the table can represent absolute mass and percent of drug deposited on the actuator, throat and different stages of the ACI. For the "dome" method, the measure of deposition can be based on mass and percent deposited on the actuator, induction cone and stages of the ACI. From the table and the deposition analyses, it can be shown that different ethanol amounts in the formulation and addition of non-volatile PEG-400 can increase the administered particle size leading to the deposition of droplets higher up on the cascade impactor. For the USP throat method, due to the throat design and high exit velocity from the pMDI, a higher mass of particle deposition in the throat can be observed. The "dome" method can be used to distinguish between various pMDI formulations and quantify deposition for the region of interest in terms of molecule size (Stage 0 to Stage 2: 9 to 4.7 μm cut-off diameters). These results can be verified assaying a commercially available marketed formulation of Ventolin®-HFA by both the USP throat and "dome" methods and observing whether the proposed "dome" method can successfully predict in vitro deposition. In one embodiment of the present invention, the "dome" method, as shown in Table II, can successfully screen particles similar to the USP throat method and can also be advantageous in aiding complete droplet evaporation.

One preferred embodiment of this invention can be used to describe the effect of formulation variables on phospholipid deposition. The impactor data can be grouped based on the method selected. The throat method can detect smaller administered particle sizes with considerable ease and the "dome" method can identify the larger administered particles. Based on those principles, the following stage grouping can be used:

> For USP throat, mass or percent deposited: Stage3+Stage4+Stage5+Stage630 Stage7+Filter
>
> For "dome" method mass or percent deposited: Cone+Stage0+Stage1+Stage2

The data from the above grouping can be summarized as shown in Table II. From such grouping analysis, it can be shown that ethanol concentrations can be utilized to affect particle size distribution. In one embodiment of the invention, two formulations can be selected containing approximately 20% and 10% w/w of ethanol as the excipient and particle migration experiments can be performed on A549 cells to determine the efficacy of these formulations.

Figure 8:
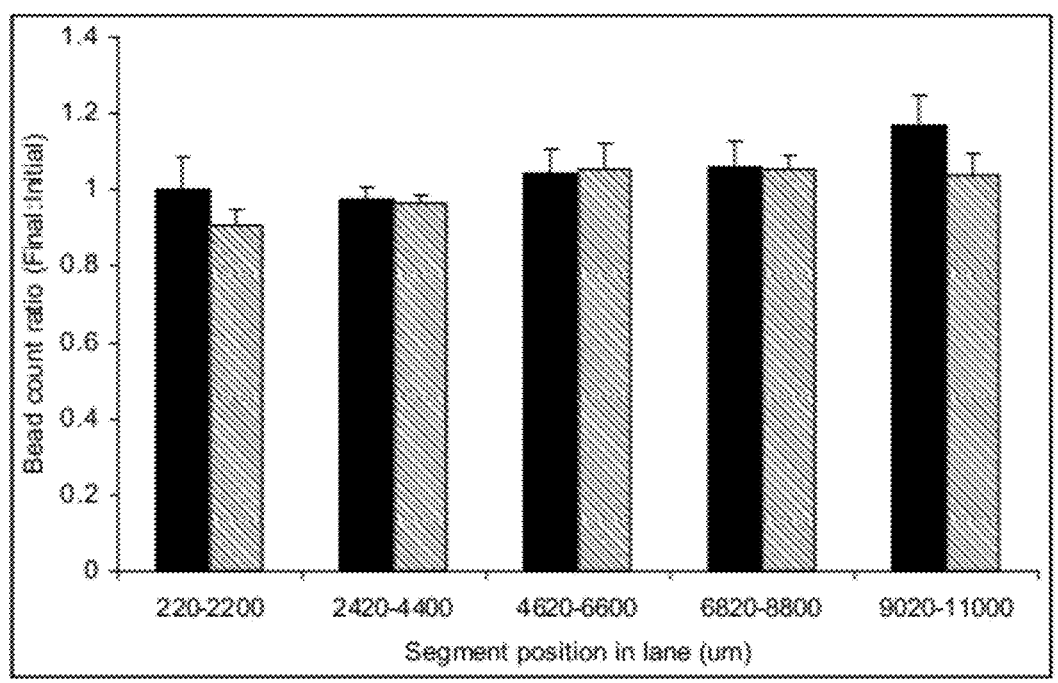
FIG. 8 provides an example of latex bead count ratio plotted as a function of grouped segment position demonstrating the effect of HFA-227 pMDI-delivered Survanta®, at a concentration of 1.5 mg/mL, on particle migration across an alveolar cell surface. The plot shows the effect of two different formulations containing 10% w/w ■ and 20% w/w ▨ of ethanol. Data represent mean±S.D. of triplicate observations with each pMDI actuated twice per observation.

The selected pMDI-formulations can be applied to A549 cells using the V-shaped 401 adaptor and migration of latex beads can be monitored as before. For these formulations containing 20% or 10% w/w ethanol (Survanta® concentration: 1.5 mg/mL), the amount of phospholipid actually deposited after exiting the slit can be determined to be 12±0.0 and 17±1.2 µg/spray respectively. Significant and similar particle migration can be observed for both these pMDI-formulations as shown in FIG. 8 ($p<0.05$). One skilled in the art understands that other tissue cells may be used.

Particle and device engineering approaches currently available employ considerable modifications of conventional aerosol formulations with the ultimate aim of generating small, slow moving particles with favorable aerodynamic properties and coordinating their release with the onset of appropriate patient inhalation. Despite such complex modifications, the high oropharyngeal deposition of drug particles cannot be avoided. The present invention takes advantage of an expanding surfactant layer, using a low cost, patient friendly, deep lung delivery technique. The present invention provides that particles can effectively be "pushed" away from the expanding surfactant layer. Spreading of localized surfactant monolayers by surface tension gradients has recently been modeled mathematically. F. F. Espinosa & R. D. Kamm, *Bolus Dispersal Through Lungs in Surfactant Replacement Therapy*, 86 J. Appl. Physiol. 391 (1999). A solid particle placed inside a fluid with a chemical gradient can move along the direction of the gradient. A. Mikhailov & D. Meinköhn, *Stochastic Dynamics, Self-Motion in Physico-Chemical Systems Far From Thermal Equilibrium* 334-345 (L. Schimansky-Geier & T. Pöschel eds., Springer, Berlin 1997). This effect takes place because the chemical substance influences the local surface tension coefficient and thus changes the intensity of surface forces applied at the liquid-solid interface. Because of this gradient in the chemical concentration, the surface tension forces acting on the particle are not balanced and the particle moves along the direction of change of the chemical concentration. The chemical gradient can be produced by a surface active agent and movement of particles away from an expanding surfactant layer will be persistent due to an asymmetrical force gradient.

Figure 9:
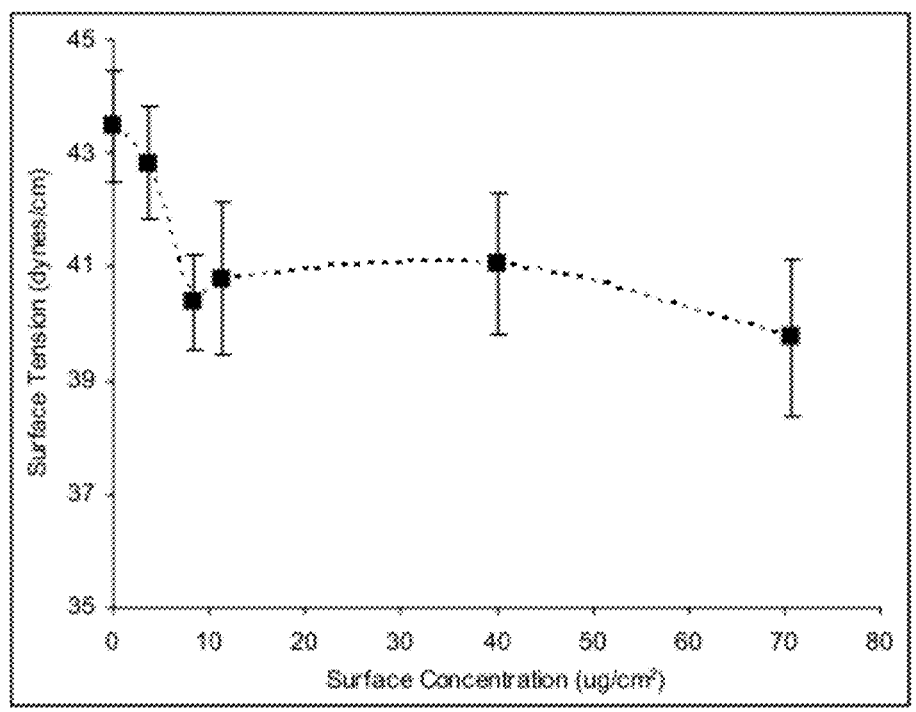
FIG. 9 describes surface tension of six selected CFC-12 containing Survanta® pMDIs administered onto Hank's balanced salt solution (surface tension 68.41±0.71 mN/m) performed using Du Noüy Tensiometer at 25° C.; vertical bars represent mean±S.D.

The measurements of surface tension due to the administered phospholipids can be conducted using the Du Noüy Tensiometer at 25° C. The force required to detach a platinum ring from the surface of HBSS (pH~7.4, surface tension 68.41±0.71 mN/m) in a petri dish can be measured for various surface concentrations of surfactant administered from the pMDIs and plotted as shown in FIG. 9. Surface tension can be shown to drop based on the surface concentration of surfactant, where one such concentration can be 11 µg/cm$^2$ ($p<0.05$) corresponding to 221 µg of administered phospholipids. This result can be correlated with particle migration data and thus movement of particles on the surface can be defined as a surface tension mediated mechanism.

In a practical scenario, such migration deeper in the lungs can occur when the aerodynamic size of deposited particles containing the phospholipids are larger than those of the previously deposited drug particles. Hence, formulations of HFA-227, for example, containing the appropriate surfactant can be developed to achieve a size slightly larger than those of the target drug.

In a broader perspective, the following dosing strategy is envisioned: (a) the patient inhales their medication from any type of FDA approved inhaler and the drug particles deposit on the luminal surface at a location which depends on the inhaler characteristics and patient technique; and (b) the patient immediately inhales a dose of the surfactant from the surfactant inhaler, such as a pMDI, containing particles or droplets larger than the drug particles or droplets. The larger particles or droplets deposit higher in the airways and then "push" drug particles deeper into the lung.

The novel phospholipid-based inhalation system of the present invention increases bioavailability of aerosolized drugs, by increasing the fraction of drug that reaches its target in the bronchioles and alveolar spaces of the lung. This approach, which is based upon fundamental theories of surface tension reduction and phenomena of surfactant spreading, requires no modification of existing drug containing inhalers but envisions the use of a second "chaser" inhaler. The "chaser" inhaler employs a mature technology to deliver surfactants with a proven history of safe use, and it is envisioned by the inventors herein that it may be useable in conjunction with all inhaled products.

TABLE II

ACI studies with selected formulations and Ventolin HFA: comparison between the USP throat method and 'dome' method. 'Sum' for throat studies = S3 + S4 + S5 + S6 + S7 + F; 'Sum' for 'dome' studies = C + S0 + S1 + S2. Data represent mean of triplicate experiments. Values show percent deposited on each stage. (Values in parentheses represent mass (µg) of drug deposited).

| Form. | Ethanol | A + S | T + C | Stage 0 | Stage 1 | Stage 2 | Stage 3 | Stage 4 | Stage 5 | Stage 6 | Stage 7 | Filter | Sum |
|---|---|---|---|---|---|---|---|---|---|---|---|---|---|
| #3 | 31.5 | 8.09 | 87.7 | 0.66 | 0.15 | 0.22 | 0.71 | 1.01 | 1.01 | 0.35 | 0.11 | 0 (0) | 3.20 |
| (Throat) | % w/w | (84.6) | (918) | (6.91) | (1.54) | (2.28) | (7.41) | (10.6) | (10.6) | (3.64) | (1.12) | | (33.3) |
| 'Dome' | | 11.6 | 12.3 | 24.4 | 17.6 | 12.4 | 11.0 | 6.21 | 2.65 | 1.15 | 0.75 | 0 (0) | 66.7 |
| | | (30.6) | (33.6) | (71.3) | (51.9) | (36.8) | (32.5) | (18.4) | (7.94) | (3.35) | (2.12) | | (194) |
| #4 | 20.8 | 11.4 | 79.5 | 1.93 | 0.44 | 0.46 | 1.33 | 1.93 | 1.91 | 0.80 | 0.28 | 0 (0) | 6.25 |
| (Throat) | % w/w | (91.9) | (641) | (15.6) | (3.57) | (3.69) | (10.7) | (15.6) | (15.4) | (6.47) | (2.23) | | (50.4) |
| 'Dome' | | 8.32 | 6.53 | 12.1 | 16.7 | 14.7 | 21.2 | 12.1 | 5.23 | 2.13 | 1.02 | 0 (0) | 50.0 |
| | | (29.0) | (23.3) | (44.0) | (61.0) | (53.1) | (75.4) | (42.8) | (18.4) | (7.59) | (3.57) | | (181) |
| #5 | 9.36 | 13.7 | 71.8 | 1.55 | 0.45 | 0.54 | 1.80 | 3.47 | 4.19 | 1.85 | 0.68 | 0 (0) | 12.0 |
| (Throat) | % w/w | (61.8) | (325) | (6.98) | (2.01) | (2.44) | (8.16) | (15.7) | (19.0) | (8.37) | (3.09) | | (54.3) |
| 'Dome' | | 6.68 | 5.01 | 2.03 | 2.89 | 6.11 | 20.6 | 28.2 | 20.7 | 5.69 | 2.07 | 0 (0) | 16.0 |
| | | (21.8) | (16.1) | (6.56) | (9.33) | (19.7) | (66.8) | (92.5) | (68.4) | (18.8) | (6.83) | | (51.7) |
| #7 | 6.56 | 14.6 | 65.0 | 1.55 | 0.52 | 0.49 | 1.87 | 5.03 | 6.64 | 3.10 | 1.16 | 0 (0) | 17.8 |
| (Throat) | % w/w | (35.9) | (160) | (3.86) | (1.15) | (1.11) | (4.72) | (12.4) | (16.5) | (7.68) | (2.86) | | (44.1) |
| 'Dome' | | 8.73 | 4.99 | 1.41 | 2.22 | 4.43 | 17.2 | 28.2 | 18.9 | 10.3 | 3.67 | 0 (0) | 13.0 |
| | | (16.2) | (9.17) | (2.60) | (4.10) | (8.22) | (31.9) | (52.3) | (35.1) | (19.1) | (6.83) | | (24.1) |

TABLE II-continued

ACI studies with selected formulations and Ventolin HFA: comparison between the USP throat method and 'dome' method.
'Sum' for throat studies = S3 + S4 + S5 + S6 + S7 + F; 'Sum' for 'dome' studies = C + S0 + S1 + S2. Data represent mean of
triplicate experiments. Values show percent deposited on each stage. (Values in parentheses represent mass (μg) of drug deposited).

| Form. | Ethanol | A + S | T + C | Stage 0 | Stage 1 | Stage 2 | Stage 3 | Stage 4 | Stage 5 | Stage 6 | Stage 7 | Filter | Sum |
|---|---|---|---|---|---|---|---|---|---|---|---|---|---|
| #8 | 7.87 | 11.1 | 85.9 | 0.96 | 0.53 | 0.42 | 0.51 | 0.37 | 0.25 | 0 (0) | 0 (0) | 0 (0) | 1.12 |
| (Throat) | % w/w | (58.6) | (441) | (5.03) | (2.74) | (2.12) | (2.58) | (1.86) | (1.22) | | | | (5.66) |
| 'Dome' | | 35.3 | 7.18 | 26.0 | 12.6 | 5.12 | 6.58 | 3.46 | 2.91 | 0.90 | 0 (0) | 0 (0) | 50.8 |
| | | (19.4) | (3.86) | (14.3) | (6.97) | (2.83) | (3.64) | (1.89) | (1.58) | (0.53) | | | (28.0) |
| #11 | 4.57 | 9.06 | 85.0 | 1.26 | 0.91 | 0.80 | 0.93 | 0.83 | 1.22 | 0 (0) | 0 (0) | 0 (0) | 2.98 |
| (Throat) | % w/w | (23.8) | (223) | (3.31) | (2.38) | (2.10) | (2.43) | (2.18) | (3.18) | | | | (7.79) |
| 'Dome' | | 30.8 | 7.45 | 25.4 | 14.1 | 6.19 | 6.71 | 4.91 | 4.42 | 0 (0) | 0 (0) | 0 (0) | 53.1 |
| | | (14.5) | (3.52) | (12.1) | (6.70) | (2.94) | (3.19) | (2.34) | (2.09) | | | | (25.2) |
| Vent. | N/A | 13.4 | 53.2 | 0.74 | 0.97 | 2.19 | 9.24 | 13.0 | 6.43 | 0.63 | 0.21 | 0 (0) | 29.5 |
| (Throat) | | (213) | (849) | (11.8) | (15.6) | (35.0) | (147) | (206) | (101) | (9.99) | (3.25) | | (468) |
| 'Dome' | | 11.6 | 3.79 | 1.39 | 2.62 | 7.01 | 29.5 | 32.2 | 10.7 | 0.87 | 0.30 | 0 (0) | 14.8 |
| | | (117) | (37.1) | (14.1) | (26.9) | (71.7) | (299) | (320) | (106) | (8.64) | (2.91) | | (150) |

What is claimed is:

1. A method for delivering medications to bronchioles and alveoli pulmonary targets comprising:
   a first step of administering aerosolized medication into a patient's respiratory tract via a nebulizer comprising a medication, wherein said nebulizer is configured to deliver the medication in a medication spray having a medication particle size distribution; and
   a second step of administering an aerosolized surfactant formulation into the patient's respiratory tract by the nebulizer comprising a surfactant formulation, wherein said the nebulizer is configured to deliver the surfactant formulation in a surfactant spray having a surfactant particle size distribution that is larger than the medication particle size distribution.

2. The method of claim 1, wherein the surfactant aerodynamic particle size distribution is greater than 5 μm.

3. The method of claim 1, wherein the surfactant formulation has a phospholipid concentration between 0.001 mg and 50 mg per administration.

4. The method of claim 3, wherein the surfactant formulation has a phospholipid concentration between 0.01 mg and 10 mg per administration.

5. The method of claim 1, wherein the surfactant formulation has a phospholipid concentration of 82-111 μg per administration.

6. The method of claim 5, wherein the surfactant formulation has a phospholipid concentration of 95-105 μg per.

7. A method for delivering medications to bronchioles and alveoli pulmonary targets comprising:
   a first step of administering aerosolized medication into a patient's respiratory tract dry powder inhaler comprising a medication, wherein said dry powder inhaler is configured to deliver the medication in a medication spray having a medication particle size distribution; and
   a second step of administering an aerosolized surfactant formulation into the patient's respiratory tract by a surfactant canister or a nebulizer comprising a surfactant formulation, wherein said a surfactant canister or the nebulizer is configured to deliver the surfactant formulation in a surfactant spray having a surfactant particle size distribution that is larger than the medication particle size distribution.

8. The method of claim 7, wherein the surfactant aerodynamic particle size distribution is greater than 5 μm.

9. The method of claim 7, wherein the surfactant formulation has a phospholipid concentration between 0.001 mg and 50 mg per spray.

10. The method of claim 7, wherein the surfactant formulation has a phospholipid concentration between 0.01 mg and 10 mg per spray.

11. The method of claim 7, wherein the surfactant formulation has a phospholipid concentration of 82-111 μg per spray and the propellant is CFC-12.

12. The method of claim 7, wherein the surfactant formulation has a phospholipid concentration of 95-105 μg per spray and the propellant is HFA-227.

* * * * *